US009681983B2

(12) United States Patent
Lind

(10) Patent No.: US 9,681,983 B2
(45) Date of Patent: Jun. 20, 2017

(54) DEBRIS CLEARANCE SYSTEM FOR AN OCULAR IMPLANT

(71) Applicant: Alcon Research, Ltd., Fort Worth, TX (US)

(72) Inventor: Casey Lind, Orange, CA (US)

(73) Assignee: Novartis AG, Basel (CH)

( * ) Notice: Subject to any disclaimer, the term of this patent is extended or adjusted under 35 U.S.C. 154(b) by 266 days.

(21) Appl. No.: 14/208,201

(22) Filed: Mar. 13, 2014

(65) Prior Publication Data

US 2015/0257930 A1 Sep. 17, 2015

(51) Int. Cl.
*A61F 9/00* (2006.01)
*A61F 9/007* (2006.01)

(52) U.S. Cl.
CPC ................................ *A61F 9/00781* (2013.01)

(58) Field of Classification Search
CPC ........................... A61M 27/00; A61F 9/00781
See application file for complete search history.

(56) References Cited

U.S. PATENT DOCUMENTS

| | | | |
|---|---|---|---|
| 4,089,329 | A | 5/1978 | Couvillon et al. |
| 4,206,762 | A | 6/1980 | Cosman |
| 4,457,757 | A | 7/1984 | Molteno |
| 4,656,827 | A | 4/1987 | Puillet |
| 4,750,901 | A | 6/1988 | Molteno |
| 4,869,282 | A | 9/1989 | Sittler et al. |
| 4,922,913 | A | 5/1990 | Waters et al. |
| 5,005,577 | A | 4/1991 | Frenkel |
| 5,083,742 | A | 1/1992 | Wylie et al. |
| 5,098,409 | A | 3/1992 | Stock |
| 5,178,604 | A | 1/1993 | Baerveldt et al. |
| 5,179,953 | A | 1/1993 | Kursar |
| 5,397,300 | A | 3/1995 | Baerveldt et al. |
| 5,466,233 | A | 11/1995 | Weiner |

(Continued)

FOREIGN PATENT DOCUMENTS

| | | | |
|---|---|---|---|
| DE | 4438201 | A1 | 5/1996 |
| WO | 9303665 | A1 | 3/1993 |

(Continued)

OTHER PUBLICATIONS

Bae et al. In vitro experiment of the pressure regulating valve for a glaucoma implant; J. Micromech. Microeng. 13 (2003) 613-619.*

(Continued)

*Primary Examiner* — Tatyana Zalukaeva
*Assistant Examiner* — Benjamin Klein
(74) *Attorney, Agent, or Firm* — Kenneth D. Bassinger

(57) ABSTRACT

An IOP control system for treatment of an ocular condition includes a drainage device sized for implantation into the eye of the patient, the drainage device including a fluid flow pathway to allow the flow of fluid from an inlet port to an outlet port. The drainage device also includes a flow system disposed within the drainage device and including a displaceable portion forming a part of the fluid flow pathway, the displaceable portion being displaceable via a magnetic field. An actuation system may be physically separate from the drainage device and may be configured to cooperate with the displaceable portion to displace the displaceable portion via the magnetic field to set free buildup or debris in the flow pathway.

11 Claims, 3 Drawing Sheets

104
102
131
122
129
130
118
140
120
134
80
126
124
136
140

(56) References Cited

U.S. PATENT DOCUMENTS 5,476,445 A 12/1995 Baerveldt et al.
5,558,629 A 9/1996 Baerveldt et al.
5,573,646 A 11/1996 Saito
5,626,558 A 5/1997 Suson
5,681,275 A 10/1997 Ahmed
5,707,643 A 1/1998 Ogura
5,910,110 A 6/1999 Bastable
6,007,511 A 12/1999 Prywes
6,048,328 A 4/2000 Haller
6,251,090 B1 6/2001 Avery
6,261,256 B1 7/2001 Ahmed
6,447,449 B1 9/2002 Fleischman
6,468,283 B1 10/2002 Richter
6,579,235 B1 6/2003 Abita
6,589,198 B1 7/2003 Soltanpour
6,682,500 B2 1/2004 Soltanpour
6,712,764 B2 3/2004 Jeffries
6,719,750 B2 4/2004 Varner et al.
6,749,568 B2 6/2004 Fleischman
6,939,299 B1 9/2005 Petersen
6,976,982 B2 12/2005 Santini et al.
7,137,952 B2 11/2006 Leonardi
7,169,106 B2 1/2007 Fleischman
7,252,006 B2 8/2007 Tai et al.
7,354,416 B2 4/2008 Quiroz-Mercado et al.
7,409,863 B2 8/2008 Bateman et al.
7,612,328 B2 11/2009 Kaiser
7,756,559 B2 7/2010 Abreu
7,824,699 B2 11/2010 Ralph et al.
8,182,435 B2 5/2012 Dacquay et al.
8,257,295 B2 9/2012 Rickard et al.
8,419,673 B2 4/2013 Rickard
9,283,115 B2 * 3/2016 Lind .................. A61F 9/00781
2001/0000527 A1 4/2001 Yaron
2002/0013545 A1 1/2002 Soltanpour et al.
2002/0019607 A1 2/2002 Bui
2002/0049374 A1 4/2002 Abreu
2002/0087111 A1 7/2002 Ethier
2002/0099359 A1 7/2002 Santini et al.
2002/0139947 A1 10/2002 Wang
2002/0143284 A1 10/2002 Tu et al.
2002/0193674 A1 12/2002 Fleischman
2003/0014036 A1 1/2003 Varner et al.
2003/0078487 A1 4/2003 Jeffries
2003/0225318 A1 12/2003 Montegrande
2004/0013702 A1 1/2004 Glover
2004/0059248 A1 3/2004 Messner
2004/0073137 A1 4/2004 Lloyd
2004/0111050 A1 6/2004 Smedley et al.
2004/0116794 A1 6/2004 Fink
2004/0147871 A1 7/2004 Burnett
2004/0186367 A1 9/2004 Fresco
2004/0254438 A1 12/2004 Chuck et al.
2004/0254517 A1 12/2004 Quiroz-Mercado et al.
2005/0049578 A1 3/2005 Tu et al.
2005/0159660 A1 7/2005 Montegrande
2005/0271704 A1 12/2005 Tu et al.
2005/0273033 A1 12/2005 Grahn
2006/0131350 A1 6/2006 Schechter
2007/0019156 A1 1/2007 Fink
2007/0032757 A1 2/2007 Medow et al.
2007/0077270 A1 4/2007 Wen
2007/0106199 A1 5/2007 Krivoy
2007/0109117 A1 5/2007 Heitzmann et al.
2007/0123767 A1 5/2007 Montegrande
2007/0129623 A1 6/2007 Fleischman
2007/0212397 A1 9/2007 Roth
2008/0015421 A1 1/2008 Penner
2008/0027478 A1 1/2008 Connors
2008/0077127 A1 3/2008 Gao et al.
2008/0097276 A1 4/2008 Bertrand et al.
2008/0125691 A1 5/2008 Yaron
2008/0129486 A1 6/2008 Jeckelmann et al.
2008/0147021 A1 6/2008 Jani
2008/0228127 A1 9/2008 Burns
2009/0069648 A1 3/2009 Irazoqui et al.
2009/0076367 A1 3/2009 Sit
2009/0143713 A1 6/2009 Van Dam et al.
2009/0227933 A1 9/2009 Karageozian
2009/0240215 A1 9/2009 Humayun et al.
2009/0275924 A1 11/2009 Lattanzio
2009/0312742 A1 12/2009 Pang
2010/0010416 A1 1/2010 Boyd
2010/0042209 A1 * 2/2010 Guarnieri ............ A61F 9/00781 623/4.1
2010/0121248 A1 5/2010 Yu et al.
2010/0174272 A1 7/2010 Weiner
2010/0222769 A1 9/2010 Meng et al.
2010/0234717 A1 9/2010 Wismer
2010/0253167 A1 10/2010 Charnley
2010/0305550 A1 12/2010 Meng et al.
2011/0046536 A1 2/2011 Stegmann
2011/0071454 A1 3/2011 Dos Santos
2011/0071456 A1 3/2011 Rickard
2011/0071458 A1 3/2011 Rickard
2011/0071459 A1 3/2011 Rickard et al.
2011/0071505 A1 3/2011 Rickard et al.
2011/0192473 A1 8/2011 Meinig et al.
2011/0248671 A1 10/2011 Santos et al.
2012/0302861 A1 11/2012 Marshall et al.

FOREIGN PATENT DOCUMENTS

WO 9803665 A1 1/1998
WO 9803809 A1 1/1998
WO 9926567 A1 6/1999
WO 9938470 A2 8/1999
WO 9938470 A3 10/1999
WO 9962586 A1 12/1999
WO WO 9966862 A1 * 12/1999 ......... A61F 9/00781
WO 0194784 A1 12/2001
WO 02056758 A1 7/2002
WO 03001991 A1 1/2003
WO 03102632 A2 12/2003
WO 2004073552 A2 9/2004
WO 2005088417 A1 9/2005
WO 2007087061 A2 8/2007
WO 2007127305 A2 11/2007
WO 2007136993 A1 11/2007
WO 2008005873 A2 1/2008
WO 2008061043 A2 5/2008
WO 2008084350 A2 7/2008
WO 2008061043 A3 9/2008
WO 2009010799 A2 1/2009
WO 2009026499 A1 2/2009
WO 2009049686 A1 4/2009
WO 2009081031 A3 9/2009
WO 2009137785 A2 11/2009
WO 2010129446 A1 11/2010
WO 2011034727 A1 3/2011
WO 2011034738 A1 3/2011
WO 2011034740 A1 3/2011
WO 2011034742 A2 3/2011
WO 2011035218 A1 3/2011
WO 2011034742 A3 5/2011
WO 2012012017 A1 1/2012

OTHER PUBLICATIONS

Sutanto et al. Design, microfabrication and testing a CMOS compatible bistable electromagnetic microvalve with latching_unlatching mechanism on a single wafer, J. Micromech. Microeng. 16 (2006) 266-275.*

Bae et al, In vitro experiment of the pressure regulating valve for a glaucoma implant, J. Micromech. Microeng. 13 (2003) 613-619.

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

Eggers, T., et al, "Wireless Intra-Ocular Pressure Monitoring System Integrated Into an Artificial Lens," 1st Annual Int'l IEEE-

(56) References Cited

OTHER PUBLICATIONS

EMBS Special Topic Conference on Microtechnologies in Medicine & Biology, Oct. 12-14, 2000, pp. 466-469, Lyon, France.
Erik Stemme and Goran Stemme; "A Valveless Diffuser/Nozzle-Based Fluid Pump"; ScienceDirect; Sensors and Actuators A, 39 (1993); pp. 159-167.
Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.
Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.
Kuppermann B D et al., 2006, "Efficacy and safety of a novel intravitreous dexamethasone drug-delivery system after applicator or incisional placement in patients with macular edema", IOVS, 47 ARVO E-Abs 5913.
Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.
Leonardi, Matteo, et al., "A Soft Contact Lens With a Mems Strain Gage Embedded for Intraocular Pressure Monitoring," in Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.
McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Miyamoto H et al., 1997, Biodegradable scleral implant for intravitreal controlled release of fluconazole, Curr Eye Res, 16(9), 930-935.
Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.
Mruthyunjaya P et al., 2003, "An intravitreal sustained release fluocinolone acetonide device to treat severe experimental uveitis", IOVS, 44, ARVO E-Abs 4215.
Neagu Cristina R.; "A Medical Microactuator Based on an Electrochemical Principle"; Thesis at the Twente University,the Netherlands, Enschede; Aug. 28, 1998; pp. 1-162.
Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.
Puers, Robert, "Linking Sensors with Telemetry: Impact on the System Design," in Proc. 8th Int'l Conference of Solid State Sensors, Actuators, Eurosens, Jun. 25-29, 1995, pp. 169-174, Stockholm, Sweden.
Ratanapakorn T et al., 2005, "Helical intravitreal triamcinolone implant: An explanation survival study", IVOS 46 E-Abs 484.
Rego MGR et al., 2004, "In vitro evaluation of sustained-release intravitreal dexamethasone implants", IOVS, 45 E-Abs 5060.
Sakurai E et al., 2001, "Scleral plug of biodegradable polymers containing ganciclovir for experimental cytomegalovirus retinitis", IOVS, 42(9), 2043-2048.
Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; Trans Am Ophthalmol Soc 2009; 107; pp. 60-71.
Schnakenberg, U., et al, "Initial Investigations on Systems for Measuring Intraocular Pressure," Sensors and Actuators, 2000, p. 287-291, vol. 85, Elsevier Science B.V., Germany.
See R F et al., 2006, "Safety and drug release profile of injectable intravitreal sustained-release fluocinolone acetonide device", IOVS, 47, ARVO E-Abs 5119.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Sutanto, et al., Design, microfabrication and testing of a CMOS compatible bistable electromagnetic microvalve with latching/unlatching mechanism on a single wafer, J. Micromech. Microeng. 16 (2006) 266-275.
Tano R et al., 2005, Helical intravitreal implant: surgical method development and outcomes, IOVS, 46, ARVO E-Abs 483.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.
Varner S E et al., 2003, "Development of a minimally invasive intravitreal implant for drug delivery", IOVS, 44, ARVO E-Abs 4214.
Walter, Peter; Intraocular Pressure Sensor: Where Are We—Where Will We Go? Journal Graefe's Archive for clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine.
Weiner A L, 2007, "Drug Delivery Systems in Ophthalmic Applications, in: Ocular Therapeutics; Eye on New Discoveries; T. Yorio, A. Clark, M.Wax, Eds, Elsevier Press/Academic Press, New York", pp. 7-43.
Yasukawa T et al., 2001, "Biodegradable scleral plugs for vitreoretinal drug delivery", Adv. Drug Del Rev., 52(1), 25-36.

* cited by examiner

DEBRIS CLEARANCE SYSTEM FOR AN OCULAR IMPLANT

FIELD OF THE INVENTION

The present disclosure relates generally to implants for treating an ocular condition and more particularly, to systems and methods for clearing debris that may clog or prevent desired operation of the implant.

BACKGROUND

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

FIG. 1 is a diagram of the front portion of an eye that helps to explain the processes of glaucoma. In FIG. 1, representations of the lens 10, cornea 20, iris 30, ciliary body 40, trabecular meshwork 50, and Schlemm's canal 60 are pictured. Anatomically, the anterior segment of the eye includes the structures that cause elevated IOP which may lead to glaucoma. Aqueous humor fluid is produced by the ciliary body 40 which lies beneath the iris 30 and adjacent to the lens 10 in the anterior segment of the eye. This aqueous humor washes over the lens 10 and iris 30 and flows to the drainage system located in the angle of the anterior chamber. The angle of the anterior chamber, which extends circumferentially around the eye, contains structures that allow the aqueous humor to drain. The trabecular meshwork 50 is commonly implicated in glaucoma. The trabecular meshwork 50 extends circumferentially around the anterior chamber. The trabecular meshwork 50 seems to act as a filter, limiting the outflow of aqueous humor and providing a back pressure that directly relates to IOP. Schlemm's canal 60 is located beyond the trabecular meshwork 50. Schlemm's canal 60 is fluidically coupled to collector channels (not shown) allowing aqueous humor to flow out of the anterior chamber. The two arrows in the anterior segment of FIG. 1 show the flow of aqueous humor from the ciliary body 40, over the lens 10, over the iris 30, through the trabecular meshwork 50, and into Schlemm's canal 60 and its collector channels.

One method of treating glaucoma includes implanting a drainage device in a patient's eye. The drainage device includes a pathway through which aqueous flows from the anterior chamber in the eye to a drainage site, relieving excessively high IOP pressure. In some instances however, over the course of treatment with the drainage device, debris or deposits may accumulate or build-up in the flow pathway. These debris and deposits may eventually decrease the flow capacity of the drainage device. This in turn may decrease the effectiveness of the drainage device as a treatment for elevated IOP.

The system and methods disclosed herein overcome one or more of the deficiencies of the prior art.

SUMMARY

In an exemplary aspect, the present disclosure is directed to an IOP control system for treatment of an ocular condition of a patient. The IOP control system may include a drainage device sized for implantation into the eye of the patient, and the drainage device may include a housing including an inlet port and an outlet port, a fluid flow pathway extending through the housing from the inlet port to the outlet port to allow the flow of fluid from the inlet port to the outlet port, and a flow system disposed within the drainage device and including a displaceable portion forming a part of the fluid flow pathway, the displaceable portion being displaceable via a magnetic field. An actuation system may be physically separate from the drainage device and may be configured to cooperate with the displaceable portion to overextend the displaceable portion via the magnetic field to set free buildup or debris in the flow pathway.

In an aspect, the displaceable portion comprises a first base layer and a second metallic layer connected with the base layer. In an aspect, the displaceable portion comprises a flexible membrane, the metallic layer being carried on the flexible membrane. In an aspect, the flow system includes a chamber with an opening to an outlet from the chamber, the displaceable portion being disposed in a position opposite the opening to the outlet. In an aspect, the flow system includes a boss, the outlet extending through the boss. In an aspect, the actuation system is an electromagnetic magnet. In an aspect, the flow pathway includes a region of minimum spacing thickness, the displaceable portion forming a part of the region of minimum spacing thickness. In an aspect, the displaceable portion is biased to a position that blocks fluid flow through the outlet. In an aspect, the housing comprises a chamber, the displaceable portion being disposed within the chamber.

In an exemplary aspect, the present disclosure is directed to an IOP control system for treatment of an ocular condition. The IOP control system may include a drainage device sized for implantation into the eye of the patient. The drainage device may include a fluid flow pathway extending through the housing from the inlet port to the outlet port to allow the flow of fluid from the inlet port to the outlet port; and may include a flow system disposed within the drainage device and configured to regulate flow of aqueous humor through the fluid flow pathway. The flow system may include a displaceable portion forming a portion of the fluid flow pathway. The displaceable portion may be responsive to pressure changes to increase and decrease the cross-sectional area of the fluid flow pathway. The flow system may also include a magnetic portion carried on the displaceable portion, the magnetic portion configured to be responsive to a magnetic field to move the displaceable portion to increase and decrease the cross-sectional area of the fluid flow pathway.

In an exemplary aspect, the present disclosure is directed to a method of clearing buildup or debris in an ocular implant. The method may include directing aqueous humor fluid flow along a fluid pathway in the ocular implant past a constriction in the fluid flow pathway adjacent a displaceable portion at a first position; displacing the displaceable portion to a second position to increase the width of the fluid flow pathway at the constriction so that buildup or debris received at the constriction adjacent the displaceable portion advances along the fluid flow pathway; and allowing the displaceable portion to return toward the first position.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
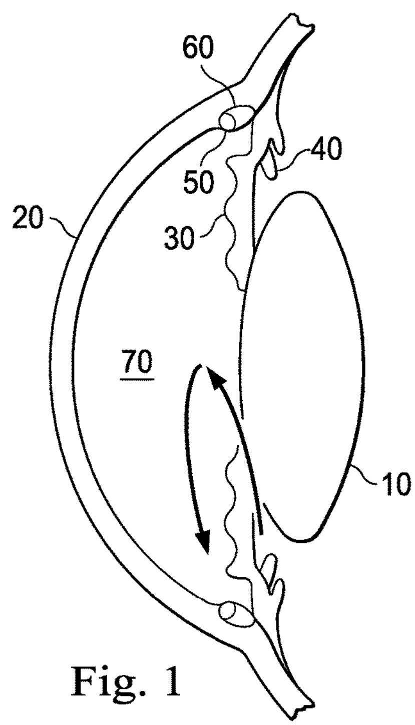
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to methods and an IOP control system arranged to permit flow from an anterior chamber of the eye to a drainage site. The system provides a system that may be used to loosen and flush buildup and debris that accumulate in an implant of the IOP control system. The system includes a displaceable flow limiter in an ocular implant that may be displaced by an external actuation system. In some examples, this includes using a magnet as the external actuation system and a magnetic material on the flow limiter. When the flow limiter is displaced by the magnetic field generated by the magnet, buildup and accumulated debris are free to flush or advance through the implant toward the drainage site. Removal of the external actuation system allows the implant to return to its prior state, without the inhibiting buildup or debris.

Figure 2:
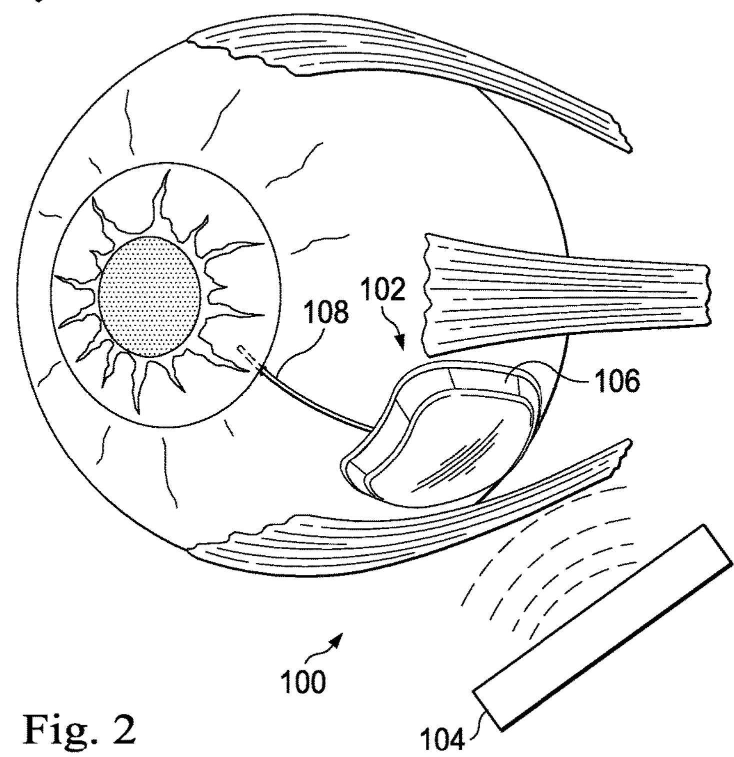
FIG. 2 is an illustration of an exemplary IOP control system according to the principles of the present disclosure.

FIG. 2 shows an exemplary system 100 for treating an ocular condition. The system 100 includes an ocular implant 102 and a remotely disposed external actuation system 104. The ocular implant 102 may be implantable within an eye according to one exemplary aspect of the present disclosure, and in the embodiment shown, is disposed on the globe of an eye. The implant 102 includes a body referred to herein as a plate 106 and a drainage tube 108 that extends from the plate 106. The plate 106 is arranged to carry various components of an IOP control system, and may include a valve, pump, transducers or sensors, processing system and memory, drug delivery components, a power source or other components that may be used to either control the implant 102 or otherwise treat ocular conditions. As shown, the drainage device 102 includes a single hollow drainage tube 108. Other embodiments include a plurality of tubes or a plurality of lumens cooperating together to permit fluid to flow through the drainage device 102. Aqueous humor may drain through the drainage device 102 from the anterior chamber 70 to the drainage site to alleviate elevated intraocular pressure conditions.

The drainage device 102 is sized to extend from the anterior chamber 70 (FIG. 1) of the eye to a drainage site in the eye, thereby bridging the anterior chamber 70 and the drainage site to provide an auxiliary flow path for aqueous humor, bypassing the flow-resistive conventional pathway through the trabecular meshwork and shunting aqueous humor directly to the drainage site.

The plate 106 is configured to fit at least partially within the subconjunctival space and is sized for example within a range between about 15 mm×12 mm to about 30 mm×15 mm and has a thickness less than about 2 mm thick and preferably less than about 1 mm thick. The plate 106 may be formed to the radius of the eye globe (about 0.5 inches). It may be rigid and preformed with a curvature suitable to substantially conform to the globe or it may be flexible to conform to the globe. Some embodiments are small enough that conforming to the globe provides little benefit in comfort or implantation technique. The above dimensions are exemplary only, and other sizes and arrangements are contemplated.

When implanted, the plate 106 may be located in the subconjunctival pocket between the conjunctiva and sclera. It may be generally located on an ocular quadrant commonly used for conventional glaucoma drainage devices with plates; that is, it may be centered such that it is equidistant from the neighboring ocular muscles that define the ocular quadrant chosen for implantation. The drainage tube 108 is sized to bridge the anterior chamber and the plate 106 in the subconjunctival pocket to provide an auxiliary flow path for aqueous humor, bypassing the flow-resistive conventional pathway through the trabecular meshwork and shunting aqueous humor directly to a drainage site.

The external actuation system 104 is separate from and arranged to be spaced apart from the eye. As is described in greater detail below, the external actuation system 104 generates and emits a magnetic field, such as for example, a static magnetic field or electromagnetic field that may be received at the drainage device 102. As will be explained below, the magnetic field may cooperate with the implant 102 to actuate a flow control portion of the implant to clear build-up or debris that may otherwise affect drainage flow through the implant 102.

Figure 3:
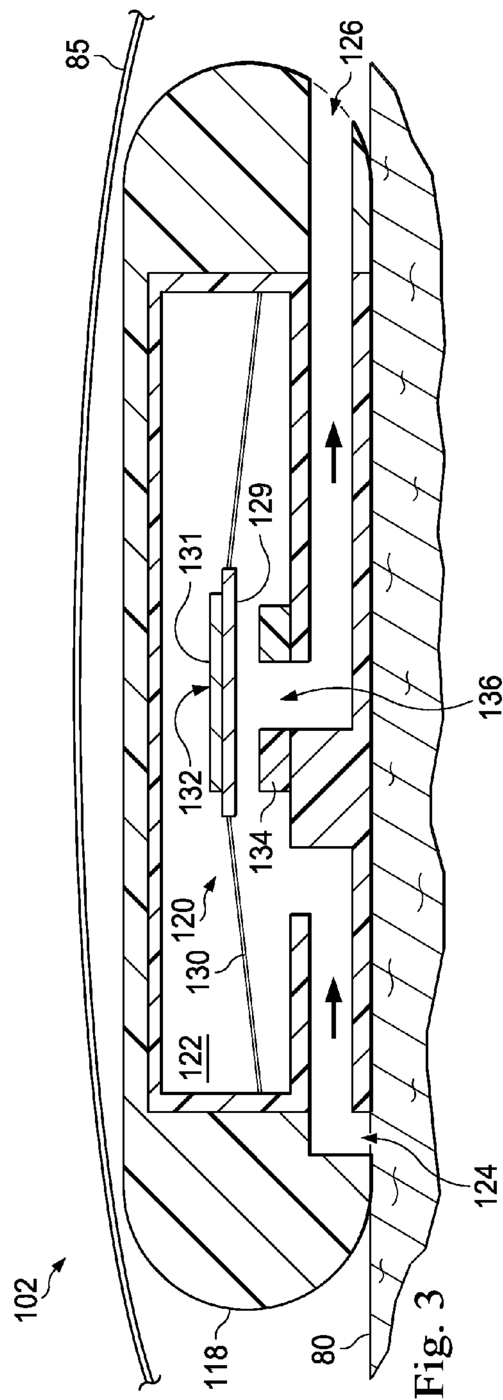
FIG. 3 is a stylized illustration of a cross-sectional view of an exemplary ocular implant according to the principles of the present disclosure.

FIG. 3 shows a stylized illustration of a cross-sectional view of a portion of the implant 102. Referring to FIG. 3, the plate 106 forms a housing 118 that includes a flow control portion 120 disposed in a central chamber 122, with an inlet 124 and an outlet 126 leading to and from the flow control chamber 122. In FIG. 3, the implant 102 is arranged so that a bottom portion of the housing 118 is adjacent the scleral wall 80 and the top portion of the implant 102 is arranged facing outward from the eye globe, and may be below the bleb wall 85.

The inlet 124 may fluidically connect to the drainage tube 108 and may receive aqueous through the drainage tube when the implant 102 is disposed within an eye of a patient.

The outlet 126 leads from the central chamber 122 to a drainage exit disposed at a drainage site.

The flow control portion 120 comprises a valve that may be used to regulate flow of aqueous through the plate 106. The flow control portion 120 comprises a valve membrane 130, a central flow limiter 132 carried by or forming a part of the membrane 130, and an elevated portion 134 that is disposed to interface with or cooperate with the central flow limiter 132.

The valve membrane 130 extends from one side or surface of the chamber 122 to the other and is configured and arranged to support the central flow limiter 132. The valve membrane 130 may be formed of parylene, glass, or other material. It may be a membrane formed of an elastically deformable material including without limitation, materials such as a silicone, silicon nitride, silicone elastomer, polyimide, parylene and others. In the example shown, the valve membrane 130 is a circular material secured at its periphery to the housing 118. In other embodiments, the housing 118 and the valve membrane 130 are formed so that the membrane has a non-circular shape, including oval, substantially rectangular, or square, for example. Other shapes are also contemplated.

The central flow limiter 132 limits the flow rate of the aqueous from the chamber 122 and through the outlet 126. In the embodiment shown, the flow limiter 132 is disposed opposite an opening 136 to the outlet 126 and configured to displace relative to the opening 136 to increase and decrease the size of the fluid flow pathway leading to the outlet 126. Due to its structure and its connection with the flexible valve membrane 130, the flow limiter 132 is configured to physically displace in a manner increasing or decreasing the distance from the flow opening 136.

In the example shown the central flow limiter 132 includes a base structure 129 and a magnetic layer 131. In some embodiments, the base structure 129 is formed of a structure different than the structure of the membrane 130. In some examples, the base structure 129 may be formed of the same material as the membrane but may have a different thickness. In some examples, the base structure 129 may be formed of a material different than the material of the membrane. In some examples, the base structure 129 has the same structure as, and is merely a portion of, the membrane 130.

The magnetic layer 131 is formed of a material having magnetic properties, such as a ferrous metal, for example. In some embodiments, the magnetic layer 131 is magnetized while in other embodiments, the magnetic layer 131 is merely responsive to magnetic fields. The magnetic layer 131 may be deposited onto or may otherwise be connected with the base structure 129 and then the base structure 129 may be connected to or may form a part of the flexible membrane 130.

The elevated portion 134 is optional and serves as a seat or stable structure that cooperates with the central flow limiter 132 to regulate or control flow through the flow control portion 120. In this embodiment, the elevated portion 134 is a boss extending into the chamber 122. The opening 136 to the outlet 126 is disposed in the boss through the surface facing the central flow limiter 132. When pressure in the inlet 124 is greater than pressure in the outlet 126, the pressure pushes the central flow limiter 132 away from the elevated portion 134. This permits aqueous to flow from the inlet 126 and chamber 122 through the opening 136 to the outlet 124, providing IOP pressure relief. Likewise, when the pressures become more equal, the biased nature of the flexible membrane 130 results in the central flow limiter 132 coming closer to and potentially resting on the elevated portion 134, thereby covering the outlet path and reducing or eliminating flow through the flow control portion 120. In this manner, the flow control portion 120 helps regulate IOP and maintain IOP in acceptable limits.

FIG. 3 shows the flow control portion 120 in a regular operational drainage state. In this condition, aqueous flows through the flowpath formed by the inlet 124, the chamber 122, and the outlet 126. As can be seen, during regular operational drainage, the region adjacent the central flow limiter 132 is also a region of minimum spacing thickness, meaning in this region, the width of the fluid flow pathway may be minimal. Accordingly, this region of minimum spacing thickness in the flow pathway may act as a constriction site in the fluid flow pathway.

Figure 4:
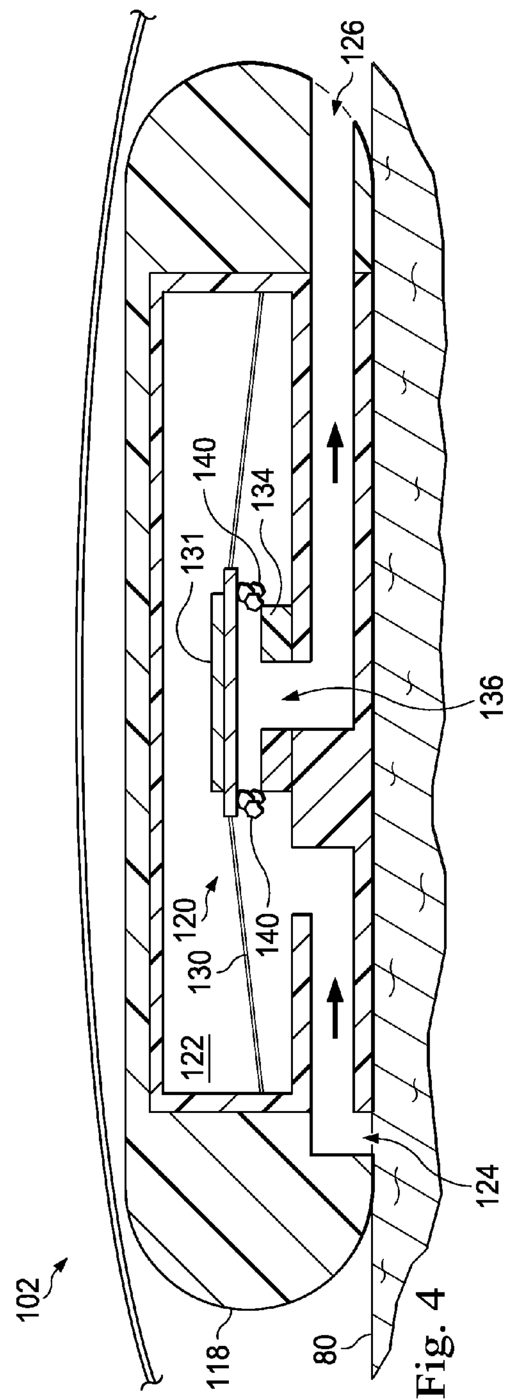
FIG. 4 is a stylized illustration of a cross-sectional view of an exemplary ocular implant according to the principles of the present disclosure.

FIG. 4 shows the portion of the implant 102 as it may appear a period of time after being implanted in a patient to control and regulate IOP. Over time, some debris or other materials may build-up or accumulate adjacent the flow limiter 132 or other portion of the membrane 130. Here, the build-up occurs in the region of minimum spacing thickness at the constriction site. In this embodiment, the build-up or debris, referenced herein by the numeral 140, is disposed adjacent the elevated portion 134. In this condition, the flow control portion 120 may lose some functionality, as the membrane 130 and the central flow limiter 132 may not be capable of responding to the fluctuating pressures on the inlet and outlet sides of the flow control portion 120. That is, the build-up or debris 140 may limit the range or motion that the flow limiter may travel.

As indicated above, the implant 102 in the embodiment in FIGS. 3 and 4 is arranged so that the bottom portion of the housing 118 is adjacent the scleral wall 80 and the top portion of the implant 102 is arranged facing outward from the eye. As such, the implant 102 is arranged so that the region of minimum spacing thickness is closer to the scleral wall 80 than is the central flow limiter 132. Accordingly, as shown in FIG. 5, when the central flow limiter displaces away from the scleral wall, the flow pathway width at the region of minimum spacing thickness increases.

Figure 5:
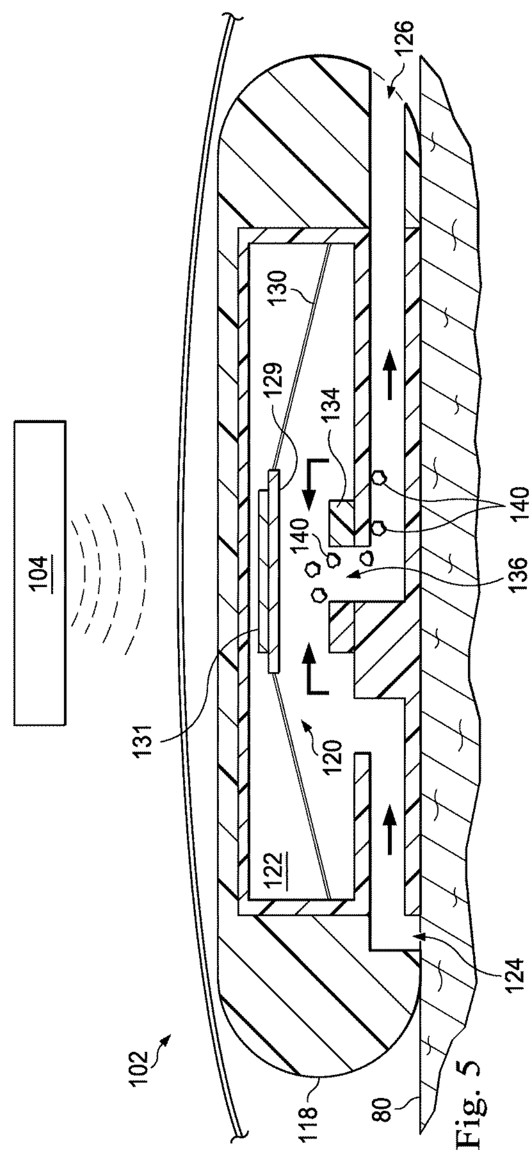
FIG. 5 is a stylized illustration of a cross-sectional view of an exemplary ocular implant according to the principles of the present disclosure.

FIG. 5 shows the operation of the system 100 in an overextended state as it clears the build-up or debris 140. In FIG. 5, the external actuation system 104 is brought into the proximity of the implant 102, and the magnetic features of the external actuation system 104 cooperate with the implant 102 to clear the build-up or debris 140. Here, the external actuation system 104 is disposed so that its magnetic field reaches to the implant 102, and more particularly, to the magnetic layer 131 of the flow limiter 132. In this embodiment, the magnetic force attracts the magnetic layer 131, fully displacing the flow limiter 132 away from the opening 136 to the outlet 126 and against the biasing force of the flexible membrane 130. In this embodiment, the magnetic field may overextend the membrane 130.

As used herein, the term "overextend" means to displace the flow limiter 132 further than when it is displaced during normal operation.

By displacing the flow limiter to such a large degree, the constriction or region of minimum spacing thickness in the flow pathway is relieved. This allows the build-up and debris 140 to freely flow across the elevated portion 134 and into the outlet 126, where it may be expelled to the drainage site. After a set period of time, such as, for example, 5 seconds or 10 seconds, or some other period of time, the user may remove the external actuation system 104 so that the metallic layer 131 is no longer in the magnetic field. When this occurs, the flow limiter 132, under the biasing load from the flexible valve membrane 130, returns to its natural state. The valve may then regulate in the manner described with reference to FIG. 3, where the valve can operate completely free from, or partially free from, interference from build-up and debris.

In some instances, the process of clearing the buildup and debris may be performed on a maintenance schedule, such as, for example, about once a month. Different period of times, both longer and shorter are also contemplated. In addition, in some instances, the external actuation system may hold open the valve for a longer period of time than described above. The period of time may be in minutes or hours if desired.

The present disclosure presents a system and method for removing build-up and debris that may impede aqueous flow or that may impede proper operation of a glaucoma drainage device. By being able to displace elements of the valve, the debris and build-up may flow through the valve, clearing it, and returning functionality to the implant. This may result in an implant with a longer useful life, reducing the likelihood that a replacement implant may be needed. This results in less cost and less inconvenience to a patient.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. An IOP control system for treatment of an ocular condition of a patient, comprising:

a drainage device sized for implantation into the eye of the patient and including:

a housing including an inlet port and an outlet port;

a fluid flow pathway extending through the housing from the inlet port to the outlet port to allow the flow of fluid from the inlet port to the outlet port; and a flow system disposed within the drainage device and including a displaceable portion forming a part of the fluid flow pathway, the displaceable portion being displaceable via a magnetic field; and an actuation system physically separate from the drainage device and configured to cooperate with the displaceable portion to overextend the displaceable portion via the magnetic field to set free buildup or debris in the flow pathway;

wherein the displaceable portion is displaceable in a first direction to an extended position by a pressure difference between an inlet pressure at the inlet port and an outlet pressure at the outlet port and is displaceable in the first direction to an overextended position by the magnetic field.

2. The IOP control system of claim 1, wherein the displaceable portion comprises a first base layer and a second metallic layer connected with the base layer.

3. The IOP control system of claim 2, wherein the displaceable portion comprises a flexible membrane, the metallic layer being carried on the flexible membrane.

4. The IOP control system of claim 1, wherein the flow system includes a chamber with an opening to an outlet from the chamber, the displaceable portion being disposed in a position opposite the opening to the outlet.

5. The IOP control system of claim 4, wherein the flow system includes a boss, the outlet extending through the boss.

6. The IOP control system of claim 1, wherein the actuation system is an electromagnetic magnet.

7. The IOP control system of claim 1, wherein the flow pathway includes a region of minimum spacing thickness, the displaceable portion forming a part of the region of minimum spacing thickness.

8. The IOP control system of claim 1, wherein the housing comprises a chamber, the displaceable portion being disposed within the chamber.

9. An TOP control system for treatment of an ocular condition of a patient, comprising:

a drainage device sized for implantation into the eye of the patient and including:

a housing including an inlet port and an outlet port;

a fluid flow pathway extending through the housing from the inlet port to the outlet port to allow the flow of fluid from the inlet port to the outlet port; and a flow system disposed within the drainage device and including a displaceable portion forming a part of the fluid flow pathway, the displaceable portion being displaceable via a magnetic field and biased to a position that blocks fluid flow through the outlet port; and an actuation system physically separate from the drainage device and configured to cooperate with the displaceable portion to overextend the displaceable portion via the magnetic field to set free buildup or debris in the flow pathway;

wherein the displaceable portion is displaceable in a first direction to an extended position by a pressure difference between an inlet pressure at the inlet port and an outlet pressure at the outlet port and is displaceable in the first direction to an overextended position by the magnetic field.

10. The IOP control system of claim 9, wherein the displaceable portion comprises a base layer and a magnetic layer disposed on the base layer.

11. The TOP control system of claim 10, wherein the base layer comprises a flexible membrane portion and a base structure, the magnetic layer being disposed on the base structure.

* * * * *